United States Patent
Benk et al.

(10) Patent No.: US 11,174,218 B2
(45) Date of Patent: Nov. 16, 2021

(54) GLYCINE PARTICLES

(71) Applicant: Merck Patent GmbH, Darmstadt (DE)

(72) Inventors: Harald Benk, Weiterstadt (DE);
Gudrun Birk, Darmstadt (DE); Melina Decker, Alsbach (DE); Dieter Lubda, Bensheim (DE); Guenter Moddelmog, Reinheim (DE); Harald Muessig, Moemlingen (DE); Tanino Scaramuzza, Hoechst (DE); Michael Schleehahn, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 23 days.

(21) Appl. No.: 16/079,340

(22) PCT Filed: Jan. 24, 2017

(86) PCT No.: PCT/EP2017/000078
§ 371 (c)(1),
(2) Date: Aug. 23, 2018

(87) PCT Pub. No.: WO2017/144149
PCT Pub. Date: Aug. 31, 2017

(65) Prior Publication Data
US 2019/0047942 A1 Feb. 14, 2019

(30) Foreign Application Priority Data
Feb. 23, 2016 (EP) .................... 16000431

(51) Int. Cl.
*C07C 229/08* (2006.01)
*B01J 2/22* (2006.01)
*A61K 9/16* (2006.01)

(52) U.S. Cl.
CPC .......... *C07C 229/08* (2013.01); *A61K 9/1617* (2013.01); *A61K 9/1682* (2013.01); *B01J 2/22* (2013.01)

(58) Field of Classification Search
None
See application file for complete search history.

(56) References Cited

U.S. PATENT DOCUMENTS

| 5,534,262 A * | 7/1996 | Dobrotvorsky ...... A61K 9/2095 424/464 |
| 6,893,664 B1 | 5/2005 | Sarphie |
| 2017/0342372 A1 * | 11/2017 | Hagen .................. C12N 5/0031 |

FOREIGN PATENT DOCUMENTS

| DE | 2622462 A1 | 12/1976 |
| DE | 69706988 T2 | 4/2002 |
| GB | 1536420 A | 12/1978 |
| JP | 11276553 A | 10/1999 |
| JP | 2014205661 A | 10/2014 |

OTHER PUBLICATIONS

Huaxue Shijie (Chemistry World), 2009, 50(4), 254).*
English Translation of (Huaxue Shijie (Chemistry World), 2009, 50(4), 254).*
International Search Report PCT/EP2017/000078 dated May 2, 2018.(pp. 1-2).
Office Action dated Feb. 15, 2021 in corresponding JP patent application JP2018562404 (pp. 1-9).

* cited by examiner

*Primary Examiner* — Sudhakar Katakam
*Assistant Examiner* — Jennifer C Sawyer
(74) *Attorney, Agent, or Firm* — Millen, White, Zelano and Branigan, P.C.

(57) ABSTRACT

The present invention relates to compacted glycine granules, where at least 75% of the granules have a particle size of above 0.7 mm, and to a process for the preparation and use of granules of this type.

13 Claims, 1 Drawing Sheet

GLYCINE PARTICLES

The present invention relates to compacted glycine granules whose particle size is above 0.7 mm, and to a process for the preparation and use of granules of this type.

Glycine (aminoacetic acid) is an a-amino acid which is not chiral and is thus also not optically active. Gylcine is typically obtained as a colourless, crystalline solid which is readily water-soluble. The melting point is about 234° C. (decomposition).

Glycine fulfils important functions in many metabolic processes, in particular as a constituent of many proteins, such as, for example, the connective tissue protein collagen, as a component for the synthesis of haem or in the function as neurotransmitter in the central nervous system.

Glycine is employed, for example, in food supplements or in biochemical buffer systems. Glycine is frequently also used as a component in nutrient formulations for use in intensive medicine and in biotechnological nutrient media. Glycine is frequently required in large amounts for these areas of application.

For industrial further processing, glycine must be in free-flowing form in order that it can easily be removed from transport containers and can be treated without problems in the machines for the preparation of the desired formulations. However, such severe lump formation or even complete caking (monoblock formation) of the material repeatedly occurs in the containers—irrespective of the size and type—that it can no longer be removed from the containers in free-flowing form. This causes the users considerable problems in the course of production, since the caked material must first be mechanically comminuted again (which is no longer possible in practice in the case of some types of container). This caking in some cases takes place after storage for only a few weeks.

The object of the present invention was therefore to find a way of providing glycine powder in a storage-stable and flowable form.

It has been found that the particle size of glycine powder has a very considerable influence on its storage stability. Glycine having a particle size of at least 0.7 mm exhibits virtually no caking, even on long storage. It remains flowable for significantly longer than powder having a smaller particle size. In addition, the dissolution rate in water is approximately the same compared with powder product in spite of the larger particle size.

The present invention therefore relates to glycine granules where at least 75% (w/w) of the glycine granules have a particle size of at least 0.7 mm. In a preferred embodiment, 85%, particularly preferably 90%, in particular 95%, of the granules have a particle size of at least 0.7 mm.

In a preferred embodiment, 80%, particularly preferably 90%, in particular 95%, of the granules have a particle size of at least 0.8 mm.

In a particularly preferred embodiment, 80%, particularly preferably 90%, in particular 95%, of the granules have a particle size of at least 1 mm.

In a preferred embodiment, the glycine granules have a bulk density of less than or equal to 0.9 g/ml, preferably between 0.5 and 0.8 g/ml.

In a preferred embodiment, the glycine granules have a tapped density of less than or equal to 1 g/ml, preferably between 0.6 and 0.9 g/ml.

In a further preferred embodiment, the glycine granules have a drying loss of not greater than 0.3%, preferably not greater than 0.2%, particularly preferably not greater than 0.1%.

In a preferred embodiment, the glycine granules are flowable after storage for 3, preferably 6, particularly preferably 12 months in a closed container at room temperature. The atmospheric humidity of the environment during storage is preferably between 20 and 30% RH.

The present invention also relates to glycine granules where at least 75% (w/w) of the glycine granules have a particle size of at least 0.7 mm, which can be prepared by compaction.

In a preferred embodiment, 85%, particularly preferably 90%, in particular 95%, of the granules have a particle size of at least 0.7 mm.

In a preferred embodiment, 80%, particularly preferably 90%, in particular 95%, of the granules have a particle size of at least 0.8 mm.

In a particularly preferred embodiment, 80%, particularly preferably 90%, in particular 95%, of the granules have a particle size of at least 1 mm.

The percentage data here in each case relate to the weight of the granules (w/w).

In a preferred embodiment, the preparation is carried out by
a) provision of glycine
b) compaction of the glycine from step a) in a roller compactor.

The glycine provided is typically in powder form. Preferably, the particle size of at least 75% (w/w) of the powder particles is below 0.7 mm.

In a preferred embodiment, the pressing force of the roller compactor in step b) is between 1 and 50 KN/cm of roller width.

In a particularly preferred embodiment, the preparation is carried out by
a) provision of glycine
b) compaction of the glycine from step a) in a roller compactor, giving a compact which comprises particles having a particle size above 0.7 mm.
c) At least partial recycling of glycine particles from the compact obtained in step b) that have a particle size smaller than 0.7 mm to the glycine provided in step a).

In a further preferred embodiment, the recycling in step c) is carried out by crushing the compacts and classification by particle size, where at least some of the glycine particles that have a particle size smaller than 0.7 mm are recycled to the glycine provided in step a).

The present invention also relates to a process for the preparation of glycine granules where at least 75% (w/w) of the glycine granules have a particle size of at least 0.7 mm, by
a) provision of glycine powder
b) compaction of the glycine powder from step a).

In a preferred embodiment, the compaction is carried out in a roller compactor.

In a particularly preferred embodiment, the preparation is carried out by
a) provision of glycine powder
b) compaction of the glycine powder from step a) in a roller compactor, giving a compact which comprises glycine particles having a particle size above 0.7 mm, preferably greater than 1 mm.
c) At least partial recycling of glycine particles from the compact obtained in step b) that have a particle size smaller than 0.7 mm to the glycine powder provided in step a).

In a preferred embodiment, the pressing force of the roller compactor in step b) is between 1 and 50 KN/cm of roller width.

In a further preferred embodiment, the recycling in step c) is carried out by crushing the compacts and classification by particle size, where at least some of the glycine particles that have a particle size smaller than 0.7 mm are recycled to the glycine provided in step a).

The invention accordingly also relates to glycine granules which can be prepared by the process according to the invention.

The present invention also relates to the use of glycine granules where at least 75% (w/w) of the glycine granules have a particle size of at least 0.7 mm, in particular the glycine granules compacted in accordance with the invention, for the preparation of nutrient media for medical applications or in biotechnology.

In addition to the individual embodiments mentioned above, the invention can also be carried out in any combination of two or more of the embodiments given above and below.

In accordance with the invention, compaction or compacting of solids means the preparation of particles of a solid which are larger in relation to the starting material by compressing the starting material under pressure. The compaction is carried out without addition of water or other solvents. It is dry compaction. The compaction can be carried out, for example, in roller compactors, eccentric tablet presses or rotary presses. In accordance with the invention, the compaction is preferably carried out in roller compactors.

Roller compactors are also called roller presses or roll presses. These are pressing machines having two preferably counterrotating rollers. The rollers have a certain separation from one another and thus form a gap. The material to be compacted is forced through this gap. Gap width and length of the rollers or the gap formed vary depending on the model. Furthermore, the rollers can be arranged vertically, horizontally or tilted. The rollers can have a profile or preferably have a smooth or grooved surface.

The feed of the material to be compacted into the roller compactor can be carried out, for example, by means of gravity or by screws. Roller compactors which are suitable in accordance with the invention are available, for example, from Alexanderwerk, Sahut Conreur, Hosokawa or Fitzpatrick Company.

In accordance with the invention, classification denotes the separation of a disperse solid mixture into fractions by particle size. Classification is preferably carried out by means of sieving. Alternative classification methods are classification or vibration. The result of a classification are at least two fractions which differ in that the minimum limit of the particle size of one fraction is at the same time the maximum limit of the other fraction. Solids particles which lie precisely in between are called limit-size particles. This is, however, an idealised consideration of the separation process. In practice, in particular in the case of powders classified by sieving, transition regions of various size exist between the classes.

Sieving is a mechanical separation process for size separation (classification) of bulk materials or disperse solids mixtures. For this purpose, the material to be separated is placed on a sieve, which is, for example, set in rotation or shaken. The driving force for the sieving is generally gravity. In order to bring particles into contact with the sieve as often as possible, the material to be separated is moved by shaking, vibration and/or tumbling. Sieving is determined by the passage probability of a particle for a given mesh width. In industry, this is carried out, for example, using a gyratory sieve, a tumble sieving machine or vibration sieving machine. The sieves are often arranged in several sieve layers one above the other.

The size of a particle is determined by sieving. A set with sieves becoming finer and finer in the downward direction is placed one on the other here. The sample to be analysed is introduced into the uppermost sieve and the sieve set is subsequently clamped into a sieving machine. The machine then shakes or vibrates the sieve set with a certain amplitude for a certain time. If, for example, a particle does not pass through a sieve having a mesh width of 0.7 mm, the particle thus has a particle size of greater than 0.7 mm.

The result of particle size analysis by means of sieving is the particle size distribution, i.e. a frequency distribution. The usual statistical parameters, such as mean, median, percentile values, scatter or skew of distribution, can be calculated therefrom and the sample thus characterised with respect to its particle size. A particle size distribution can be narrow or broad, depending on the magnitude of the differences in particle size in a sample.

Powders are piles of solid particles. The individual particles differ through size, shape, mass and surface area. The cohesion is ensured by cohesion forces.

Powders can be crystals, amorphous substances, aggregates or agglomerates. In accordance with the invention, the term glycine powder is used for mixtures of glycine particles of which less than 75% (w/w) have a particle size of at least 0.7 mm.

Granules consist of grains or particles. The granules according to the invention consists of grains or particles of which at least 75% (w/w) have a particle size of at least 0.7 mm. The granules according to the invention preferably consist of particles or grains which are an agglomerate of powder particles. This means that the granule particles have formed by compaction of powder particles.

Granule particles typically have an asymmetrical shape.

In accordance with the invention, a powder is referred to as caked if its particles are no longer freely mobile against one another and which is therefore no longer flowable or free-flowing. This feature is typically determined visually. Whereas slightly caked powders are possibly still mobile against one another as relatively large lumps, heavily caked powders usually form a type of monolithic block. Lumps or block must, if appropriate, be mechanically destroyed in order to obtain a free-flowing powder again.

A flowable or free-flowing powder can, for example, be poured evenly out of a vessel without relatively large lumps.

Granules are storage-stable if they do not change their properties significantly over the time of their storage. For example, glycine granules are storage-stable if they remain flowable during the storage time.

It has been found that the properties of the solid glycine can be strongly influenced by changing the particle size. In particular, caking can be influenced. While glycine in the form of fine particles having a particle size below 0.5 mm, in particular below 0.1 mm, frequently tends towards uncontrolled caking, even with exclusion of moisture, this is substantially prevented by compaction of fine particles to give relatively large compact particles having a particle size of above 0.7 mm. Besides the pressing during compaction and the subsequent optional breaking-up of the flakes (granulation) and classification, the particles are preferably not subjected to any further treatment step. The compaction is carried out without addition of reagents, such as water or other solvents.

The process according to the invention for the preparation of compacted glycine is therefore typically carried out by a) provision of glycine, preferably glycine powder. This glycine powder consists of particles of which less than 75% (w/w) have a particle size of at least 0.7 mm. In general, at least 65% (w/w) of the particles of the powder have a particle size of at most 0.5 mm. Pulverulent glycine that is suitable as starting material is, for example, glycine from Merck KGaA, Germany, with the Article Number 100590.

b) Compaction of the pulverulent glycine from step a)

The compaction, i.e. the dry pressing, is preferably carried out in a roller compactor. Roller compactors are known to the person skilled in the art and are commercially available. Particularly suitable in accordance with the invention are roller compactors having a separation between the rollers of 0.5 to 3 mm, preferably between 1 and 2 mm. Roller compactors which are particularly suitable in accordance with the invention have rollers having a width between 10 and 50 cm, so that the gap between the two rollers has a length between 10 and 50 cm.

The pressing force of the roller compactor is typically between 0.1 and 100 kN/cm of roller width. The rollers are preferably pressed together with a force between 1 and 50 kN.

The feed of the glycine provided into the roller compactor preferably takes place by means of one or more screws. By pressing powders between preferably counterrotating rolls, roller compactors produce larger compacts of the powders. On use of rollers having smooth or grooved surfaces, plate-shaped, flake-form and/or lump-form compacts are frequently obtained.

The shape and size of the compacts obtained from the roller compactor is typically very irregular and can be influenced by the further processing. Merely transfer or packaging of the compacts will typically lead to partial breakage of the flakes.

The compacts obtained directly from the roller compactor are therefore preferably broken up into granules or larger particles in a further process step. This can be carried out, for example, by a roller crusher with subsequent sieving through a vibrating sieve or friction sieve, by a rotor homogenisation mill or an oscillating mill (oscillating vibration mill). Granule particles comprising pressed powder are thus obtained from the irregular, lump-form compacts. The size of the particles can be adjusted through the mesh width of the sieve. In this way, it is also possible to influence the upper limit of the particle size. Granules whose particle size is not greater than 5 mm are preferably produced.

Furthermore, the compacts or compacts broken up to give compacted particles are subsequently preferably classified. This enables a more homogeneous material with respect to the particle size to be obtained and in addition at least some of the fines content is preferably separated off. In accordance with the invention, the fines content denotes particles which have a particle size below the desired minimum particle size of, for example, 0.7 mm, 0.8 mm or 1 mm.

Depending on the performance of the compaction and/or breaking-up, granules having a low or high fines content can be obtained. In the grand case of granules having a low fines content, it is typically not necessary to separate this off. However, if this is desired or necessary in order to meet the product specification with respect to the particle size contents, classification can be carried out. In order to avoid loss of material and to re-use the fines content, the latter can be separated off and re-added to the material subjected to compaction.

The classification and performance of the recycling make it possible to determine what proportion of the particles is recycled. If particles having a particle size of below, for example, 0.7 mm are separated off during the classification, these can all be recycled. However, further sub-groups can also be produced, more precisely the particles having a particle size of, for example, below 0.7 mm can be separated off from the product, but not recycled in full, but instead, for example, only particles below 0.5 mm or below 0.2 mm. Equally, the classification can be carried out in such a way that only particles having a particle size of, for example, 0.5 mm or 0.2 mm are separated off and recycled, so the product still has a content of particles having a particle size of 0.5 mm or 0.2 mm up to, for example, 0.7 mm—so long as this proportion does not exceed the maximum fines content defined for the corresponding product.

In a preferred embodiment of the process according to the invention, all or some of the fines content is removed from the product by classification and preferably continuously mixed again in its entirety with the material provided in step a) and thus fed to the compaction step again. This recycling reduces the fines content in the desired compacted product without the need to accept a loss of material.

It has been found that granules of glycine have a significantly lower tendency to cake if they consist of particles of which at least 75% (w/w) have a particle size of at least 0.7 mm. The granules have preferably been produced by means of compaction. They particularly preferably have a fines content of less than 20%, particularly preferably less than 10% (w/w).

Figure 1:
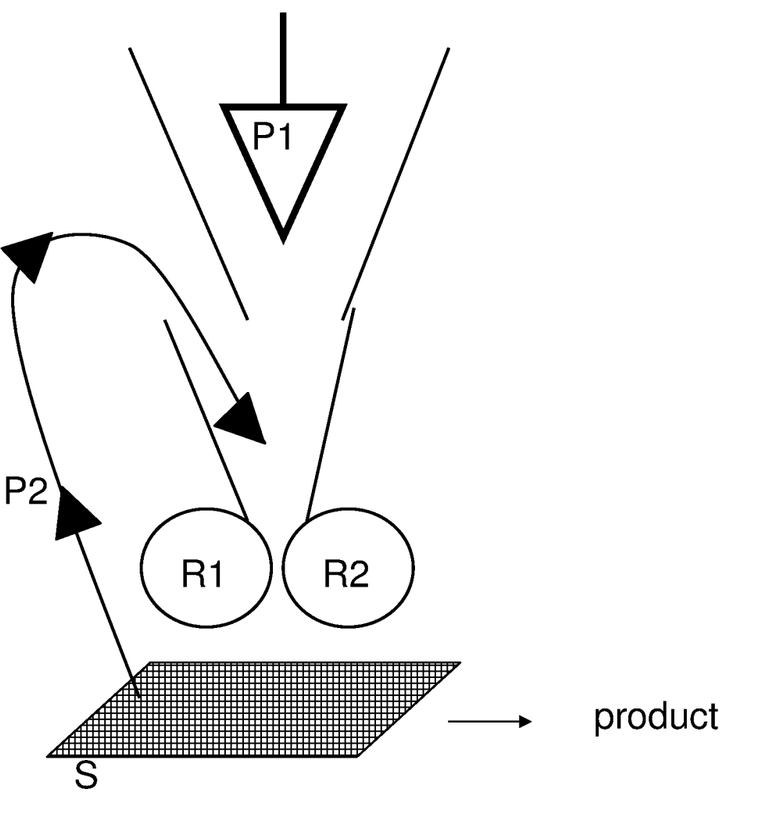
FIG. 1 shows diagrammatically a possible arrangement for carrying out the process according to the invention.

FIG. 1 shows diagrammatically a possible arrangement for carrying out the process according to the invention. The roller compactor is depicted with rollers R1 and R2. The glycine powder P1 is fed to the roller compactor from a reservoir by means of gravity. Alternatively, a transport screw not depicted in FIG. 1 can also be used for this purpose. The compacted product released from the roller compactor is broken up and classified by means of a grinding and sieving device, depicted as sieve S. The desired product fraction is removed for further use and optionally packaging and the fines content P2, which has a particle size below, for example, 0.7 mm, is fed continuously back to the pulverulent glycine, which is introduced into the roller compactor.

The present invention also relates to glycine granules where at least 75% (w/w) of the glycine granules have a particle size of at least 0.7 mm.

This glycine is preferably prepared by means of compaction. This glycine is therefore also called compacted glycine granules below. This glycine preferably has a fines content of less than 20%, particularly preferably less than 10% (w/w).

These compacted glycine granules are preferably obtainable by the process according to the invention.

In a preferred embodiment, the compacted glycine granules have a bulk density of less than or equal to 0.9 g/ml, preferably between 0.5 and 0.8 g/ml.

In a preferred embodiment, the compacted glycine granules have a tapped density of less than or equal to 1 g/ml, preferably between 0.6 and 0.9 g/ml.

In a further preferred embodiment, the compacted glycine granules have a drying loss of not greater than 0.3%, preferably not greater than 0.2%, particularly preferably not greater than 0.1%.

In a further embodiment, the compacted glycine granules have a Hausner factor of less than or equal to 1.18 and a compressibility index of less than or equal to 15%.

In particular, it has surprisingly been found that the storage stability of the compacted glycine granules is significantly better than that of the pulverulent starting material. While the pulverulent starting material cakes after only a few weeks and is thus no longer flowable, the compacted glycine granules cake significantly less and/or significantly later. For example, the compacted glycine granules do not cake at all on open storage for 7 weeks at 25° C. and 60% RH, whereas the pulverulent material cakes after only one week. Further comparisons under different storage conditions are given in the examples.

It has been found that the compacted glycine granules remain flowable after storage over 3, preferably 6, particularly preferably 12 months in a sealed container at room temperature. The atmospheric humidity of the environment during the storage is between 20 and 30% RH. The container is preferably sealed in an air-tight manner. In this way, the storage stability can, if desired, be increased still further. A container is any type of packaging which is suitable for the storage of powders or granules and can be sealed. Containers of this type are known to the person skilled in the art. Preferred containers are screw-lid containers made of glass or plastic, such as, for example, made from PE, PE sacks, big bags or plastic drums.

This is surprising, in particular, since glycine is not very hygroscopic both as powder and also as compact and compacted glycine is no less hygroscopic (see experiments on the hygroscopicity).

Furthermore, the compacted glycine granules exhibit a similar dissolution behaviour to pulverulent glycine. This means that compacted glycine granules can be brought into solution just as quickly as pulverulent, uncompacted glycine under the same conditions.

The present invention also relates to the use of the compacted glycine granules for the preparation of nutrient media for medical applications or in biotechnology. Examples of nutrient media of this type are, in particular, injection solutions, infusion solutions and cell culture media. Nutrient media of this type are typically in the form of a solids mixture or aqueous solution. The compacted glycine granules can be added to the media in the form of a solid or can be dissolved in water or another solvent and then added to the nutrient media. Processes for the preparation of nutrient media are known to the person skilled in the art. The components of the nutrient medium are preferably mixed and ground in solid form. They are subsequently dissolved by addition of water or an aqueous buffer. Whereas hygroscopic or unstable components may have to be stored and brought into solution separately, the compacted glycine granules can readily be processed with the other stable components.

The present invention also relates to a process for increasing the storage stability of glycine powder, in particular for retaining the flowability of glycine. In this process, glycine powder is compacted to give glycine granules, where at least 75% (w/w) of the glycine granules obtained have a particle size of at least 0.7 mm.

The preferred embodiments of the preparation process of compacted glycine granules mentioned above apply here. The process can be carried out at room temperature. The glycine granules obtained by means of the process have a significantly higher storage stability than the glycine powder employed as starting material. In particular, the flowability is maintained for longer compared with glycine powder under identical storage conditions.

The processes according to the invention are simple and effective to carry out. Without a chemical change to the glycine, the properties of the glycine can be modified purely by mechanical actions, such as pressing and optionally sieving. In particular, a significant increase in the storage stability takes place, since the material according to the invention cakes significantly more slowly and remains flowable for longer.

Even without further comments, it is assumed that a person skilled in the art will be able to utilise the above description in the broadest scope. The preferred embodiments and examples should therefore merely be regarded as descriptive disclosure which is absolutely not limiting in any way.

The complete disclosure content of all applications, patents and publications mentioned above and below, in particular the corresponding EP 16000431.3, filed on 23 Feb. 2016, is incorporated into this application by way of reference.

EXAMPLES

A) Equipment and Methods for Characterisation of the Substance Properties
1. Bulk density: in accordance with DIN EN ISO 60: 1999 (German version)
   figures in "g/ml"
2. Tapped density: in accordance with DIN EN ISO 787-11: 1995 (German version)
   figures in "g/ml"
3. Compressibility index: in accordance with 2.9.36. Powder Flow Ph Eur 8.0 (English version)
   figures in "%"
4. Hausner factor: in accordance with 2.9.36. Powder Flow Ph Eur 8.0 (English version)
   dimensionless
5. Particle size determination by dry sieving through a sieve tower:
   Retsch AS 200 control, Retsch (Germany); amount of substance: about 110.00 g; sieving time: 30 minutes; amplitude intensity: 1 mm; interval: 5 seconds; analytical sieves with metal wire mesh in accordance with DIN ISO 3310
   sieve widths (in µm) for comparison 1 and 2: 1000, 710, 600, 500, 400, 355, 300, 250, 200, 150, 100, 50, 32
   sieve widths (in µm) for Example A, B, C, D, E and F: 2000, 1700, 1600, 1400, 1250, 1120, 1000, 900, 800, 710, 600, 500
   Indication of the amount distribution per sieve fraction in the tables as "% by weight of the sample weight"
6. Determination of the drying loss:
   Determination according to Ph Eur 8.6 in accordance with glycine monograph: dry 1.000 g of substance at 105° C. for 2 hours in the oven (Ph Eur 8.6 under 2.2.32.)
   figures in "% by weight"
7. DVS conditions (determination of the hygroscopicity):
   Surface Measurement Systems Ltd. UK 1996-2007, Method: 0-98% RH, 10% steps, 25° C., 0.0005 wt %-min., halfcycle.sao; performance of the measurement in accordance with manufacturer's instructions
   increase in weight figures in "% by weight"
8. Dissolution rate:
   Equipment used: Mettler AT201 balance, 150 ml beaker, IKA® RCT basic magnetic stirrer plate, 50 ml measuring cylinder, stirrer bar diameter 7 mm and length 4 cm, stirring speed 200 rpm, amount of substance 4.00 g+/−0.1 g, DI water with a temperature between 20 and 25° C. ("DI water" is "deionised water");
   Procedure: place 50 ml of DI water in the beaker and switch on the stirrer. Place the thermometer in the DI water, add the substance and measure the time (stopwatch) until the substance has visually dissolved without a residue.
   figures in "seconds"
9. Storage conditions in climatic cabinets:
   a) Comparisons 1 and 2 and Examples E and F: in each case 160 g+/−5 g of substance are stored at 25° C./60% RH and 40° C./75% RH both open (in a glass dish) and also closed (in a screw-lid glass container)—the caking is assessed after a storage time of 1, 2 and 7 weeks.
   Glass dish: diameter 95 mm, height 55 mm, the substance is distributed over the dish base in a uniform layer thickness; the assessment is carried out by tilting the dish and visually observing the flow behaviour depending on the tilt angle (in some cases, however, the samples have already caked so much that free powder flow can no longer be observed)
   screw-lid glass container: 250 ml, height 11.5 cm, outside diameter 7 cm, white glass tightly sealed with plastic screw lid, the assessment is carried out by tilting the glass and visually observing the flow behaviour depending on the tilt angle (in some cases, however, the samples have already caked so much that free powder flow can no longer be observed—in these cases, after rotation of the glass through 180°, the glycine remains adhering to the glass base or only deposits in part)

b) Examples A, B, C and D: in each case 120 g+/−5 g of substance are stored at 40° C./75% RH both open (in a glass dish) and also closed (in a screw-lid glass container)—the caking is assessed after a storage time of 2 and 7 weeks.

Glass dish: diameter 95 mm, height 55 mm, the substance is distributed over the dish base in a uniform layer thickness; the assessment is carried out by tilting the dish and visually observing the flow behaviour depending on the tilt angle (in some cases, however, the samples have already caked so much that free powder flow can no longer be observed)

screw-lid glass container: 250 ml, height 11.5 cm, outside diameter 7 cm, white glass tightly sealed with plastic screw lid, the assessment is carried out by tilting the glass and visually observing the flow behaviour depending on the tilt angle (in some cases, however, the samples have already caked so much that free powder flow can no longer be observed—in these cases, after rotation of the glass through 180°, the glycine remains adhering to the glass base or only deposits in part)

10. Weight changes after storage
weight change figures in "g" compared with the initial value at the beginning of storage 11. "Break energy" determination:
REVOLUTION powder analyzer (Mercury Scientific Inc, Newton, USA); rotation rate 0.3 rpm, test method FlowMethod_SP.fam; drum diameter 100 mm; amount of powder 95-100 ml
figures in "mJ"

12. "Avalanche angle" determination:
REVOLUTION powder analyzer (Mercury Scientific Inc, Newton, USA); rotation rate 0.3 rpm, test method FlowMethod_SP.fam; drum diameter 100 mm; amount of powder 95-100 ml
figures in degrees ("°")

B) Working Methods

Commercially available crystalline pulverulent glycine (Article 100590 glycine cryst. Suitable for use as excipients EMPROVE® exp Ph Eur, BP, JP, USP from Merck KGaA, Darmstadt, Germany) is subjected to dry granulation over roller compactors with subsequent crushing and sieving via an oscillating sieve mill.

Two different compactors are used:

1. Examples A to D: model RC 100 compactor from powtec Maschinen and Engineering, Remscheid, Germany; roller diameter 100 mm, roller width 30 mm, grooved roller surface, no roller cooling, sieve mesh width 3 mm, undersized particle sieving 1 mm without material recycling; the gap width arises through the roller pressure selected 2. Examples E and F: model K200/100 compactor with FC 400 sieve mill from Hosokawa Bepex, Leingarten, Germany; roller diameter 200 mm, roller width 100 mm, grooved roller surface, no roller cooling, sieve mesh width 2 mm; undersized particle sieving 1 mm with material recycling; the gap width arises through the roller pressure selected The comparison against the prior art takes place against 2 batches of a commercially available crystalline pulverulent glycine from Merck KGaA, Darmstadt (Germany), article 100590 glycine cryst.

1. Examples A, B, C and D: preparation of a compacted glycine having improved flowability and storage stability (compacted glycine having coarse fractions >2000 μm prepared under various roller pressures)

Compaction Example A:
speed of rotation of screw 30 rpm, speed of rotation of rollers 5 rpm, pressure at the pressure rollers 5.23+/−0.33 KN/cm Compaction Example B:
speed of rotation of screw 30 rpm, speed of rotation of rollers 5 rpm, pressure at the pressure rollers 6.54+/−0.33 KN/cm Compaction Example C:
speed of rotation of screw 20 rpm, speed of rotation of rollers 4 rpm, pressure at the pressure rollers 7.84+/−0.33 KN/cm Compaction Example D:
speed of rotation of screw 30 rpm, speed of rotation of rollers 5 rpm, pressure at the pressure rollers 3.92+/−0.33 KN/cm rpm=revolutions per minute Bulk Density, Tapped Density, Carr Index:
(details on the measurement methods, see under Methods)

| Sample | Bulk density (g/ml) | Tapped density (g/ml) | Hausner factor | Compressibility index (%) | Drying loss (%) |
|---|---|---|---|---|---|
| Example A | 0.72 | 0.82 | 1.14 | 12.7 | 0.02 |
| Example B | 0.72 | 0.82 | 1.13 | 11.4 | 0.04 |
| Example C | 0.72 | 0.80 | 1.12 | 10.5 | 0.05 |
| Example D | 0.73 | 0.82 | 1.12 | 10.6 | 0.04 |

Particle Distribution Determined by Tower Sieving:
Figures in % by weight (details on the measurement method, see under Methods)

| Sample | <500 μm | 500-600 μm | 600-710 μm | 710-800 μm | 800-900 μm | 900-1000 μm | 1000-1120 μm |
|---|---|---|---|---|---|---|---|
| Example A | 2.4 | 0.5 | 0.9 | 1.9 | 4.9 | 4.0 | 7.0 |
| Example B | 1.2 | 0.2 | 0.6 | 1.5 | 4.2 | 3.8 | 7.1 |
| Example C | 2.2 | 0.7 | 1.3 | 2.3 | 6.1 | 4.8 | 8.6 |
| Example D | 2.2 | 0.5 | 1.0 | 1.8 | 4.7 | 4.0 | 7.2 |

| Sample | 1120-1250 μm | 1250-1400 μm | 1400-1600 μm | 1600-1700 μm | 1700-2000 μm | >2000 μm |
|---|---|---|---|---|---|---|
| Example A | 8.0 | 8.9 | 15.3 | 7.4 | 22.7 | 16.1 |
| Example B | 8.6 | 9.8 | 15.6 | 7.1 | 22.2 | 18.1 |
| Example C | 10.6 | 11.0 | 14.5 | 6.6 | 19.2 | 12.1 |
| Example D | 7.7 | 8.0 | 15.1 | 6.4 | 22.6 | 18.8 |

2. Examples E and F: preparation of a compacted glycine having improved flowability and storage stability (compacted glycine having a low coarse content >2000 μm)

Compaction Example E and F:

Speed of rotation of screw 17 to 19 rpm,

Speed of rotation of rollers 21 rpm, pressure at the pressure rollers 9.15+/−0.65 KN/cm 2 samples were taken and characterised: Example E and Example F Bulk Density, Tapped Density, Hausner Factor, Compressibility Index:
(details on the measurement methods, see under Methods)

| Sample | Bulk density (g/ml) | Tapped density (g/ml) | Hausner factor | Compressibility index (%) | Drying loss (%) |
|---|---|---|---|---|---|
| Example E | 0.72 | 0.80 | 1.12 | 10.6 | 0.03 |
| Example F | 0.72 | 0.81 | 1.12 | 10.4 | 0.03 |

Particle Distribution Determined by Tower Sieving:
Figures in % by weight (details on the measurement method, see under Methods)

| Sample | <500 μm | 500-600 μm | 600-710 μm | 710-800 μm | 800-900 μm | 900-1000 μm |
|---|---|---|---|---|---|---|
| Example E | 0.2 | 0.2 | 0.1 | 0.5 | 1.6 | 4.2 |
| Example F | 0.4 | 0.0 | 0.2 | 0.5 | 1.5 | 4.3 |

| Sample | 1000-1120 μm | 1120-1250 μm | 1250-1400 μm | 1400-1600 μm | 1600-1700 μm | 1700-2000 μm | >2000 μm |
|---|---|---|---|---|---|---|---|
| Example E | 9.7 | 12.1 | 13.5 | 25.2 | 13.1 | 19.4 | 0.2 |
| Example F | 11.2 | 14.0 | 15.7 | 26.1 | 10.8 | 15.3 | 0.0 |

3. Comparisons 1 and 2: commercially available crystalline glycine 2 batches of a commercially available glycine are employed for comparative purposes (as prior art)

Comparison 1: Glycine cryst. suitable for use as excipient EMPROVE® exp Ph. Eur., BP, JP, USP Art. No. 1.00590.9025; batch: VP708290

Comparison 2: Glycine cryst. suitable for use as excipient EMPROVE® exp Ph. Eur., BP, JP, USP Art. No. 1.00590.9025; batch: VP709890

Bulk Density, Tapped Density, Hausner Factor, Compressibility Index:
(details on the measurement methods, see under Methods)

| Sample | Bulk density (g/ml) | Tapped density (g/ml) | Hausner factor | Compressibility index (%) | Drying loss (%) |
|---|---|---|---|---|---|
| Comparison 1 | 1.01 | 1.15 | 1.14 | 12.5 | 0.02 |
| Comparison 2 | 1.03 | 1.26 | 1.23 | 18.4 | 0.02 |

Although both comparisons exhibit a very low water content and also comparable bulk and tapped densities, they differ in the level of the Hausner factor and in the compressibility index (in accordance with Ph Eur 6th Edition, Table 2.9.36-2 "Scale of flowability", comparison 1 should be classified as "good" comparison 2 as "satisfactory")—in the visual assessment, comparison 2 already exhibits slight caking tendencies compared with comparison 1, but where the agglomerates can be destroyed by slight application of pressure.

Particle Distribution Determined by Tower Sieving:
Figures in % by weight (details on the measurement method, see under Methods)

| Sample | <32 μm | 32-50 μm | 50-100 μm | 100-150 μm | 150-200 μm | 200-250 μm | 250-300 μm | 300-355 μm |
|---|---|---|---|---|---|---|---|---|
| Comparison 1 | 0.0 | 0.5 | 1.5 | 5.3 | 6.0 | 8.6 | 12.9 | 8.5 |
| Comparison 2 | 0.0 | 5.6 | 6.7 | 8.5 | 9.3 | 12.3 | 15.8 | 8.2 |

| Sample | 355-400 μm | 400-500 μm | 500-600 μm | 600-710 μm | 710-1000 μm | >1000 μm |
|---|---|---|---|---|---|---|
| Comparison 1 | 8.2 | 17.0 | 15.9 | 8.6 | 7.0 | 0.0 |
| Comparison 2 | 8.9 | 13.3 | 7.7 | 2.6 | 1.1 | 0.0 |

C) Results
Summary of the Experimental Results
1. Glycine (examples according to the invention and comparisons) exhibit an identical behaviour in the change in mass in the DVS; only from >90% RH is any increase in the mass evident at all, i.e. the material—irrespective of whether examples according to the invention or comparisons—is virtually non-hygroscopic up to 90% RH. The increases in weight at 98% RH even exhibit a slightly lower uptake of water for the rapidly caking comparisons 1 and 2 compared with the stable Examples A-F.
2. Changes in the drying losses after stress loading are not evident—all samples (examples according to the invention and comparisons) behave the same and exhibit no hygroscopicity
3. In spite of this missing tendency for the uptake of water, the samples surprisingly exhibit clear differences in their flow behaviour on storage under stress loading: whereas Examples A to F remain flowable, comparisons 1 and 2 cake after only a very short time and can no longer be removed in free-flowing form from the storage vessels—this even applies to comparison 1 with its very good initial value with respect to the flow behaviour.
4. Experiments and comparisons show that the compacted glycine with its particular particle size >700 μm remains flowable for significantly longer than the comparative material, even after storage under stress conditions, i.e. elevated temperature and atmospheric humidity.
5. The dissolution behaviour of Example A to F is virtually unchanged, even after storage, and has a sufficient rate for problem-free further processing Experimental Results in Detail
1) Hygroscopicity (DVS)
Both Examples A to F according to the invention and comparisons 1 and 2 only exhibit an increase in weight (DVS) from a rel. humidity of >90%. At a rel. humidity of 98%, the compacted and non-lumping Examples A to E even have a tendency towards a slightly greater increase in weight than comparisons 1 and 2.

DVS Measurement (Dynamic Vapor Sorption):

|  | Relative humidity (%) | | | | | | | | | | |
|---|---|---|---|---|---|---|---|---|---|---|---|
|  | 0.0 | 10.0 | 20.0 | 30.0 | 40.0 | 50.0 | 60.0 | 70.0 | 80.0 | 90.0 | 98.0 |
| Example A | 0.00 | 0.00 | 0.00 | 0.00 | 0.00 | 0.00 | 0.01 | 0.01 | 0.01 | 0.03 | 2.29 |
| Example B | 0.00 | 0.00 | 0.00 | 0.00 | 0.01 | 0.01 | 0.01 | 0.01 | 0.02 | 0.03 | 3.25 |
| Example C | 0.00 | 0.00 | 0.00 | 0.00 | 0.00 | 0.01 | 0.01 | 0.01 | 0.02 | 0.04 | 2.70 |
| Example D | 0.00 | 0.00 | 0.01 | 0.01 | 0.01 | 0.01 | 0.01 | 0.02 | 0.02 | 0.03 | 3.15 |
| Example E | 0.00 | 0.00 | 0.00 | 0.00 | 0.00 | 0.00 | 0.01 | 0.01 | 0.01 | 0.02 | 2.49 |
| Example F | 0.00 | 0.00 | 0.00 | 0.00 | 0.00 | 0.00 | 0.01 | 0.01 | 0.01 | 0.02 | 2.86 |
| Comparison 1 | 0.00 | 0.00 | 0.00 | 0.00 | 0.00 | 0.01 | 0.01 | 0.01 | 0.01 | 0.01 | 1.83 |
| Comparison 2 | 0.00 | 0.00 | 0.00 | 0.00 | 0.00 | 0.00 | 0.00 | 0.00 | 0.01 | 0.02 | 1.40 |

Increases in weight figures in "% by weight"
2) Drying Losses after Storage Under Stress Conditions
Figures in % by weight
Storage condition: 25° C./60% RH open storage

| Sample | Initial value | after 1 week | after 2 weeks | after 7 weeks |
|---|---|---|---|---|
| Example A |  | no storage takes place | | |
| Example B |  | no storage takes place | | |
| Example C |  | no storage takes place | | |
| Example D |  | no storage takes place | | |
| Example E | 0.03 | 0.05 | 0.05 | 0.09 |
| Example F | 0.03 | 0.09 | 0.02 | 0.09 |
| Comparison 1 | 0.02 | 0.07 | 0.01 | 0.04 |
| Comparison 2 | 0.02 | 0.05 | 0.04 | 0.02 |

Storage condition: 25° C./60% RH closed storage

| Sample | Initial value | after 1 week | after 2 weeks | after 7 weeks |
|---|---|---|---|---|
| Example A |  | no storage takes place | | |
| Example B |  | no storage takes place | | |
| Example C |  | no storage takes place | | |
| Example D |  | no storage takes place | | |
| Example E | 0.03 | 0.06 | 0.03 | 0.08 |
| Example F | 0.03 | 0.08 | 0.06 | 0.10 |
| Comparison 1 | 0.02 | 0.01 | 0.02 | 0.04 |
| Comparison 2 | 0.02 | 0.05 | 0.03 | 0.02 |

Storage condition: 40° C./75% RH open storage

| Sample | Initial value | after 1 week | after 2 weeks | after 7 weeks |
|---|---|---|---|---|
| Example A | 0.02 | — | 0.01 | 0.02 |
| Example B | 0.04 | — | 0.04 | <0.01 |
| Example C | 0.05 | — | <0.01 | 0.01 |
| Example D | 0.04 | — | <0.01 | <0.01 |
| Example E | 0.03 | 0.06 | 0.03 | 0.08 |
| Example F | 0.03 | 0.04 | 0.04 | 0.07 |
| Comparison 1 | 0.02 | 0.01 | 0.01 | 0.04 |
| Comparison 2 | 0.02 | 0.04 | 0.03 | 0.03 |

Storage condition: 40° C./75% RH closed storage

| Sample | Initial value | after 1 week | after 2 weeks | after 7 weeks |
|---|---|---|---|---|
| Example A | 0.02 | — | <0.01 | <0.01 |
| Example B | 0.04 | — | 0.04 | <0.01 |
| Example C | 0.05 | — | <0.01 | 0.01 |
| Example D | 0.04 | — | 0.02 | 0.025 |
| Example E | 0.03 | 0.01 | 0.03 | 0.08 |
| Example F | 0.03 | 0.08 | 0.04 | 0.09 |
| Comparison 1 | 0.02 | 0.03 | 0.02 | 0.04 |
| Comparison 2 | 0.02 | 0.05 | 0.02 | 0.03 |

3) Changes in Weight after Storage Under Stress Conditions

| Sample | Difference [g] after 1 week | Difference [g] after 2 weeks | Difference [g] after 7 weeks |
|---|---|---|---|
| Example A | | no storage takes place | |
| Example B | | no storage takes place | |
| Example C | | no storage takes place | |
| Example D | | no storage takes place | |
| Example E | 0.01 | −0.03 | 0.00 |
| Example F | −0.02 | 0.03 | 0.00 |
| Comparison 1 | 0.00 | −0.01 | 0.04 |
| Comparison 2 | 0.01 | 0.07 | 0.08 |

Storage condition: 25° C./60% RH closed storage

| Sample | Difference [g] after 1 week | Difference [g] after 2 weeks | Difference [g] after 7 weeks |
|---|---|---|---|
| Example A | | no storage takes place | |
| Example B | | no storage takes place | |
| Example C | | no storage takes place | |
| Example D | | no storage takes place | |
| Example E | −0.01 | −0.02 | 0.00 |
| Example F | −0.01 | −0.01 | 0.01 |
| Comparison 1 | 0.00 | −0.01 | −0.02 |
| Comparison 2 | 0.04 | 0.08 | 0.00 |

Storage condition: 40° C./75% RH open storage

| Sample | Difference [g] after 1 week | Difference [g] after 2 weeks | Difference [g] after 7 weeks |
|---|---|---|---|
| Example A | — | 0.01 | 0.00 |
| Example B | — | 0.00 | −0.01 |
| Example C | — | −0.01 | −0.01 |
| Example D | — | 0.00 | −0.02 |
| Example E | 0.04 | 0.00 | 0.04 |
| Example F | −0.01 | 0.03 | −0.02 |
| Comparison 1 | −0.02 | 0.03 | 0.00 |
| Comparison 2 | 0.02 | 0.02 | −0.04 |

Storage condition: 40° C./75% RH closed storage

| Sample | Difference [g] after 1 week | Difference [g] after 2 weeks | Difference [g] after 7 weeks |
|---|---|---|---|
| Example A | — | −0.02 | −0.03 |
| Example B | — | −0.02 | −0.03 |
| Example C | — | 0.01 | −0.04 |
| Example D | — | 0.00 | −0.04 |
| Example E | 0.07 | −0.02 | 0.00 |
| Example F | −0.03 | −0.01 | −0.02 |
| Comparison 1 | 0.03 | 0.01 | −0.06 |
| Comparison 2 | 0.01 | 0.03 | −0.01 |

4) Changes in the Dissolution Rates after Storage Under Stress Conditions (Figures in "Seconds")

Storage condition: 25° C./60% RH open storage

| Sample | Initial value/ day of starting storage | after 1 week | after 2 weeks | after 7 weeks |
|---|---|---|---|---|
| Example E | 318 ± 20 | 331 ± 13 | 343 ± 7 | 328 ± 19 |
| Example F | 316 ± 15 | 300 ± 7 | 341 ± 10 | 343 ± 20 |
| Comparison 1 | 233 ± 51 | 176 ± 14 | 194 ± 7 | 198 ± 6 |
| Comparison 2 | 127 ± 11 | 181 ± 8 | 185 ± 5 | 191 ± 9 |

Storage condition: 25° C./60% RH closed storage

| Sample | Initial value/ day of starting storage | after 1 week | after 2 weeks | after 7 weeks |
|---|---|---|---|---|
| Example E | 318 ± 20 | 328 ± 7 | 352 ± 8 | 358 ± 19 |
| Example F | 316 ± 15 | 301 ± 13 | 339 ± 6 | 363 ± 25 |
| Comparison 1 | 233 ± 51 | 176 ± 13 | 216 ± 6 | 207 ± 20 |
| Comparison 2 | 127 ± 11 | 173 ± 6 | 209 ± 5 | 196 ± 5 |

Storage condition: 40° C./75% RH open storage

| Sample | Initial value/ day of starting storage | after 1 week | after 2 weeks | after 7 weeks |
|---|---|---|---|---|
| Example A | 358 ± 12 | — | 335 ± 11 | 313 ± 5 |
| Example B | 347 ± 11 | — | 340 ± 16 | 309 ± 12 |
| Example C | 339 ± 6 | — | 346 ± 18 | 324 ± 20 |
| Example D | 348 ± 5 | — | 332 ± 9 | 270 ± 10 |

| Sample | Initial value/ day of starting storage | after 1 week | after 2 weeks | after 7 weeks |
|---|---|---|---|---|
| Example E | 318 ± 20 | 336 ± 12 | 326 ± 22 | 337 ± 10 |
| Example F | 316 ± 15 | 312 ± 18 | 332 ± 13 | 330 ± 12 |
| Comparison 1 | 233 ± 51 | 192 ± 9 | 202 ± 13 | 191 ± 17 |
| Comparison 2 | 127 ± 11 | 182 ± 5 | 187 ± 6 | 209 ± 12 |

Storage condition: 40° C./75% RH closed storage

| Sample | Initial value/ day of starting storage | after 1 week | after 2 weeks | after 7 weeks |
|---|---|---|---|---|
| Example A | 358 ± 12 | — | 350 ± 23 | 297 ± 4 |
| Example B | 347 ± 11 | — | 332 ± 12 | 304 ± 9 |
| Example C | 339 ± 6 | — | 326 ± 10 | 299 ± 6 |
| Example D | 348 ± 5 | — | 319 ± 11 | 290 ± 1 |
| Example E | 318 ± 20 | 322 ± 8 | 343 ± 5 | 343 ± 14 |
| Example F | 316 ± 15 | 316 ± 7 | 350 ± 15 | 342 ± 12 |
| Comparison 1 | 233 ± 51 | 177 ± 6 | 215 ± 8 | 203 ± 4 |
| Comparison 2 | 127 ± 11 | 201 ± 17 | 193 ± 10 | 215 ± 9 |

5) Clumping Behaviour after Storage Under Stress Conditions (Visual Description)

"Free-flowing"=the glycine flows freely without input of force—agglomerates are not visually evident.

"Lumpy"=the glycine exhibits individual relatively large agglomerates (and encrustations (of diameter about 1 cm), but is still free-flowing.

"Slightly caked"=the glycine is solid; however, it can be converted back into the free-flowing state by slight input of force (gentle poking with a glass rod or spatula, hitting or shaking).

"Strongly caked"=the glycine is solid; strong input of force (vigorous poking with a glass rod or spatula) is necessary in order to break up the glycine again—however, the glycine is still strongly agglomerated after this (chunk formation) and is not free-flowing.

Storage condition: 25° C./60% RH open storage

| Sample | Initial value | after 1 week | after 2 weeks | after 7 weeks |
|---|---|---|---|---|
| Example E | free-flowing | free-flowing | free-flowing | free-flowing |
| Example F | free-flowing | free-flowing | free-flowing | free-flowing |
| Comparison 1 | free-flowing | slightly caked | slightly caked | slightly caked |
| Comparison 2 | lumpy | strongly caked | strongly caked | strongly caked |

Storage condition: 25° C./60% RH closed storage

| Sample | Initial value | after 1 week | after 2 weeks | after 7 weeks |
|---|---|---|---|---|
| Example E | free-flowing | free-flowing | free-flowing | free-flowing |
| Example F | free-flowing | free-flowing | free-flowing | free-flowing |
| Comparison 1 | free-flowing | lumpy | free-flowing | slightly caked |
| Comparison 2 | lumpy | strongly caked | strongly caked | strongly caked |

Storage condition: 40° C./75% RH open storage

| Sample | Initial value | after 1 week | after 2 weeks | after 7 weeks |
|---|---|---|---|---|
| Example A | free-flowing | — | slightly caked | slightly caked |
| Example B | free-flowing | — | slightly caked | slightly caked |
| Example C | free-flowing | — | slightly caked | slightly caked |
| Example D | free-flowing | — | slightly caked | slightly caked |
| Example E | free-flowing | slightly caked | slightly caked | slightly caked |
| Example F | free-flowing | slightly caked | slightly caked | slightly caked |
| Comparison 1 | free-flowing | strongly caked | strongly caked | strongly caked |
| Comparison 2 | lumpy | strongly caked | strongly caked | strongly caked |

Storage condition: 40° C./75% RH closed storage

| Sample | Initial value | after 1 week | after 2 weeks | after 7 weeks |
|---|---|---|---|---|
| Example A | free-flowing | — | free-flowing | free-flowing (weak agglomerates) |
| Example B | free-flowing | — | free-flowing | free-flowing |
| Example C | free-flowing | — | free-flowing | free-flowing |
| Example D | free-flowing | — | free-flowing | free-flowing |
| Example E | free-flowing | free-flowing | free-flowing | free-flowing |
| Example F | free-flowing | free-flowing | free-flowing | free-flowing |
| Comparison 1 | free-flowing | strongly caked | strongly caked | strongly caked |
| Comparison 2 | lumpy | strongly caked | strongly caked | strongly caked |

6) Changes in the Flow Behaviour (Measured as Change in the "Avalanche Angle" in the Revolution Powder Analyser) after Storage Under Stress Conditions Storage condition: 25° C./60% RH open storage

| | Avalanche angle [°] | | | |
|---|---|---|---|---|
| Sample | Initial value | after 1 week | after 2 weeks | after 7 weeks |
| Example E | 43.6 | 42.5 | 41.8 | 42.1 |
| Example F | 45.6 | 43.2 | 41.9 | 42.2 |
| Comparison 1 | 39.4 | 40.8 | 39.5 | 40.2 |
| Comparison 2 | 65.6 | n.m. | n.m. | n.m. |

Storage condition: 25° C./60% RH closed storage

| | Avalanche angle [°] | | | |
|---|---|---|---|---|
| Sample | Initial value | after 1 week | after 2 weeks | after 7 weeks |
| Example E | 43.6 | 42.6 | 41.8 | 42.1 |
| Example F | 45.6 | 42.8 | 43.2 | 42.3 |
| Comparison 1 | 39.4 | 41.8 | 39.6 | 40.5 |
| Comparison 2 | 65.6 | n.m. | n.m. | n.m. |

Storage condition: 40° C./75% RH open storage

| | Avalanche angle [°] | | | |
|---|---|---|---|---|
| Sample | Initial value | after 1 week | after 2 weeks | after 7 weeks |
| Example E | 43.6 | 43.8 | 43.2 | 43.5 |
| Example F | 45.6 | 43.7 | 42.7 | 42.6 |
| Comparison 1 | 39.4 | n.m. | n.m. | n.m. |
| Comparison 2 | 65.6 | n.m. | n.m. | n.m. |

Storage condition: 40° C./75% RH closed storage

| | Avalanche angle [°] | | | |
|---|---|---|---|---|
| Sample | Initial value | after 1 week | after 2 weeks | after 7 weeks |
| Example E | 43.6 | 42.8 | 42.8 | 42.9 |
| Example F | 45.6 | 43.4 | 42.4 | 42.8 |
| Comparison 1 | 39.4 | n.m. | n.m. | n.m. |
| Comparison 2 | 65.6 | n.m. | n.m. | n.m. | n.m.=not measurable since the material has already caked too strongly in order to be removed from the vessel (too many agglomerates are present or the material has to be poked out of the dish/bottle)

7) Changes in the Flow Behaviour (Measured as Change in the "Break Energy" in the Revolution Powder Analyser) after Storage Under Stress Conditions Storage condition: 25° C./60% RH open storage

| Sample | Break energy [mJ] | | | |
| --- | --- | --- | --- | --- |
|  | Initial value | after 1 week | after 2 weeks | after 7 weeks |
| Example E | 28.4 | 28.1 | 27.7 | 27.9 |
| Example F | 28.8 | 28.6 | 28.3 | 28.2 |
| Comparison 1 | 27.4 | 27.5 | 27.2 | 27.5 |
| Comparison 2 | 33.5 | n.m. | n.m. | n.m. |

Storage condition: 25° C./60% RH closed storage

| Sample | Break energy [mJ] | | | |
| --- | --- | --- | --- | --- |
|  | Initial value | after 1 week | after 2 weeks | after 7 weeks |
| Example E | 28.4 | 28.1 | 27.7 | 27.9 |
| Example F | 28.8 | 28.5 | 28.6 | 27.9 |
| Comparison 1 | 27.4 | 28.0 | 27.1 | 27.4 |
| Comparison 2 | 33.5 | n.m. | n.m. | n.m. |

Storage condition: 40° C./75% RH open storage

| Sample | Break energy [mJ] | | | |
| --- | --- | --- | --- | --- |
|  | Initial value | after 1 week | after 2 weeks | after 7 weeks |
| Example E | 28.4 | 28.7 | 28.0 | 28.0 |
| Example F | 28.8 | 28.7 | 28.3 | 28.1 |
| Comparison 1 | 27.4 | n.m. | n.m. | n.m. |
| Comparison 2 | 33.5 | n.m. | n.m. | n.m. |

Storage condition: 40° C./75% RH closed storage

| Sample | Break energy [mJ] | | | |
| --- | --- | --- | --- | --- |
|  | Initial value | after 1 week | after 2 weeks | after 7 weeks |
| Example E | 28.4 | 28.3 | 28.4 | 28.2 |
| Example F | 28.8 | 28.9 | 28.0 | 28.5 |
| Comparison 1 | 27.4 | n.m. | n.m. | n.m. |
| Comparison 2 | 33.5 | n.m. | n.m. | n.m. | n.m.=not measurable since the material has already caked too strongly in order to be removed from the vessel (too many agglomerates are present or the material has to be poked out of the dish/bottle)

The invention claimed is:

1. A composition consisting of glycine granules, in which composition at least 75% (w/w) of the glycine granules have a particle size of at least 0.7 mm.

2. The composition consisting of glycine granules according to claim 1, in which composition at least 80% (w/w) of the glycine granules have a particle size of at least 0.8 mm.

3. The composition consisting of glycine granules according to claim 1, in which composition the glycine granules have a bulk density of less than or equal to 0.9 g/ml.

4. The composition consisting of glycine granules according to claim 1, in which composition the glycine granules are flowable after storage for 3 months in a closed container at room temperature.

5. A composition consisting of glycine granules, at least 75% (w/w) of the glycine granules in which composition the glycine granules have a particle size of at least 0.7 mm, prepared by compaction.

6. The composition consisting of glycine granules according to claim 5, prepared by a process comprising
 a) provision of glycine powder
 b) compaction of the glycine powder from step a) in a roller compactor.

7. The composition consisting of glycine granules according to claim 6, wherein the roller compactor in b) has a pressing force of 1 to 50 KN/cm of roller width.

8. The composition consisting of glycine granules according to claim 5, prepared by a process comprising
 a) provision of glycine powder
 b) compaction of the glycine powder from a) in a roller compactor, giving a compact which comprises particles having a particle size above 0.7 mm
 c) at least partial recycling of glycine particles from the compact obtained in b) that have a particle size smaller than 0.7 mm to the glycine powder provided in a).

9. The composition consisting of glycine granules according claim 8, wherein the recycling in c) is carried out by crushing the compacts and classification by particle size, where at least some of the glycine particles that have a particle size smaller than 0.7 mm are recycled to the glycine powder provided in a).

10. A process for the preparation of a composition consisting of glycine granules according to claim 1, in which composition at least 75% (w/w) of the glycine granules have a particle size of at least 0.7 mm, by
 a) provision of glycine powder
 b) compaction of the glycine powder from a).

11. The process according to claim 10, the preparation comprising
 a) provision of glycine powder
 b) compaction of the glycine powder from a) in a roller compactor, giving a compact which comprises particles having a particle size above 0.7 mm
 c) at least partial recycling of glycine particles from the compact obtained in b) that have a particle size smaller than 0.7 mm to the glycine powder provided in a).

12. The process according to claim 10, the roller compactor in b) having a pressing force of 1 to 50 KN/cm of roller width.

13. The process according to claim 10, the recycling in c) being carried out by crushing the compacts and classification by particle size, at least some of the glycine particles that have a particle size smaller than 0.7 mm being recycled to the glycine powder provided in a).

* * * * *